(12) United States Patent
Gu et al.

(10) Patent No.: US 10,499,860 B2
(45) Date of Patent: Dec. 10, 2019

(54) SYSTEMS AND METHODS FOR POSITRON EMISSION TOMOGRAPHY

(71) Applicant: SHANGHAI UNITED IMAGING HEALTHCARE CO., LTD., Shanghai (CN)

(72) Inventors: Xiaoyue Gu, Shanghai (CN); Shitao Liu, Shanghai (CN); Weiping Liu, Shanghai (CN); Yixing Sun, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 91 days.

(21) Appl. No.: 15/815,825

(22) Filed: Nov. 17, 2017

(65) Prior Publication Data

US 2019/0125280 A1 May 2, 2019

(30) Foreign Application Priority Data

Oct. 30, 2017 (CN) .......................... 2017 1 1042643

(51) Int. Cl.
| | |
|---|---|
| *G06K 9/00* | (2006.01) |
| *A61B 6/03* | (2006.01) |
| *G01T 1/29* | (2006.01) |
| *G06T 11/00* | (2006.01) |
| *A61B 5/00* | (2006.01) |
| *G01T 1/164* | (2006.01) |
| *A61B 6/00* | (2006.01) |

(52) U.S. Cl.
CPC ............ *A61B 6/037* (2013.01); *G01T 1/2985* (2013.01); *G06T 11/005* (2013.01); *A61B 5/0035* (2013.01); *A61B 6/032* (2013.01); *A61B 6/586* (2013.01); *G01T 1/1648* (2013.01)

(58) Field of Classification Search
CPC .................. A61B 6/027; G06T 11/005; G06T 2207/10081; G06T 2207/30004; G06T 5/005
USPC ......... 382/131, 128, 275; 250/363.03, 363.1, 250/370.09, 363.04, 374, 394; 600/425
See application file for complete search history.

(56) References Cited

U.S. PATENT DOCUMENTS 7,602,951 B2 * 10/2009 Hsieh .................... G06T 11/005
382/128
8,558,181 B2 * 10/2013 Gagnon ................. A61B 6/037
250/363.03
2013/0030287 A1 * 1/2013 Yamaya ................ G01T 1/2985
600/425

* cited by examiner

*Primary Examiner* — Charlotte M Baker
(74) *Attorney, Agent, or Firm* — Metis IP LLC

(57) ABSTRACT

The disclosure relates to a system and method for reconstructing a PET image. The method may include: obtaining PET data relating to an object collected by a plurality of detector units; determining functional status of the plurality of detector units; generating reconstruction data based on the functional status of the respective detector units and the PET data; and reconstructing a PET image based on the reconstruction data.

17 Claims, 11 Drawing Sheets

SYSTEMS AND METHODS FOR POSITRON EMISSION TOMOGRAPHY

CROSS-REFERENCE TO RELATED APPLICATIONS

This application claims priority of Chinese Application No. 201711042643.2 filed on Oct. 30, 2017, the entire contents of which are hereby incorporated by reference.

TECHNICAL FIELD

The application generally relates to a system and method for positron emission tomography (PET), and more specifically relates to PET image reconstruction based on detector unit working status.

BACKGROUND

Positron emission tomography (PET) is a nuclear medicine functional imaging technique that is used to observe metabolic processes in a body. A PET imaging system may include numerous detector units for detecting radiation events originating from the body. The failure of some detector units may affect acquired PET data and therefore a resultant PET image.

SUMMARY

In a first aspect of the present disclosure, a method for reconstructing a PET image is provided. The method may be implemented on at least one device each of which has at least one processor and storage. The method may include one or more of the following operations. PET data relating to an object collected by a plurality of detector units may be obtained. Functional status of the plurality of detector units may be determined. Reconstruction data may be generated based on the functional status of the respective detector units and the PET data. A PET image may be reconstructed based on the reconstruction data.

In some embodiments, a detector unit of the plurality of detector units may include one or more detector subunits.

In some embodiments, the reconstruction data may include a portion of the PET data that is collected by a first detector unit and a second detector unit of the plurality of detector units, and a unit difference between the first detector unit and the second detector unit may be less than a threshold.

In some embodiments, the method may include one or more of the following operations. The plurality of detector units may be divided into a first group and a second group based on the functional status of the respective detector units, wherein the functional status of the detector units in the first group is positive, and the functional status of the detector units in the second group is negative. The reconstruction data may be generated based on the PET data collected by the detector units in the first group.

In some embodiments, the detector units in the first group are located together and not spatially separated by a detector unit of the second group.

In some embodiments, the method may include one or more of the following operations. The detector units in the first group may be divided into a first subgroup and a second subgroup, wherein the detector units in each of the first subgroup and the second subgroup are located together and not spatially separated by a detector unit of the second group, and the number of detector units in the first subgroup is larger than the number of detector units in the second subgroup. The reconstruction data may be generated based on the PET data collected by the detector units in the first subgroup.

In some embodiments, when a detector unit of the plurality of detector units includes a plurality of detector subunits, the method may include one or more of the following operations. For each detector unit of the plurality of detector units, functional status of the respective detector subunits of a detector unit may be determined. Functional status of the detector unit may be determined based on the functional status of the plurality of detector subunits of the detector unit.

In a second aspect of the present disclosure, a system for reconstructing a PET image is provided. The system may include at least one storage medium and at least one processor. The at least one storage medium may include a set of instructions. The at least one processor may be configured to communicate with the at least one storage medium, wherein when executing the set of instructions, the system is configured to perform one or more of the following operations. PET data relating to an object collected by a plurality of detector units may be obtained. Functional status of the plurality of detector units may be determined. Reconstruction data may be generated based on the functional status of the respective detector units and the PET data. A PET image may be reconstructed based on the reconstruction data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

Figure 2:
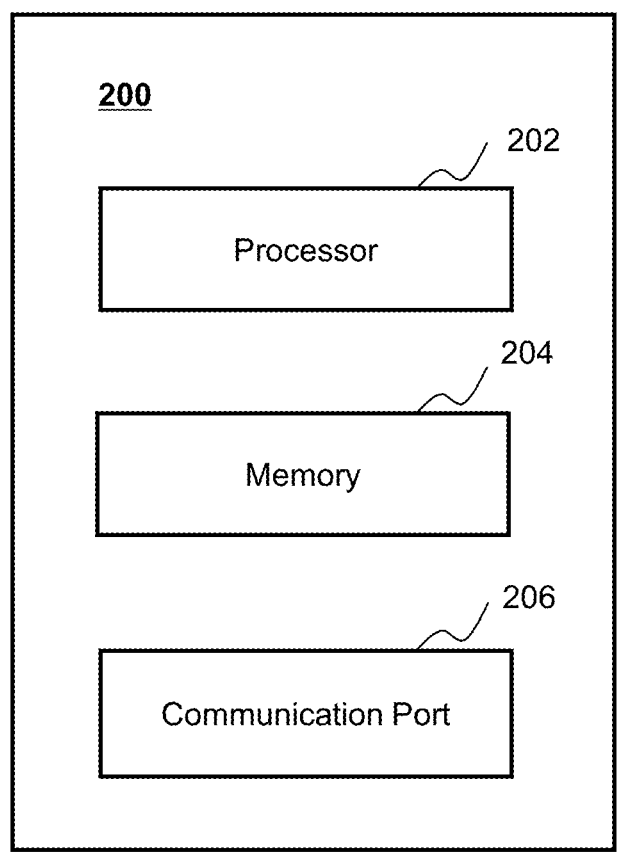
FIG. 2 is a block diagram illustrating exemplary hardware and software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 202 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnostic or research purposes. The imaging system may find its applications in different fields such as medicine or industry. For example, the imaging system may be used in internal inspection including, for example, tumor metabolism, brain function, heart function, or the like, or any combination thereof.

The following description is provided to help better understanding PET image reconstruction methods or systems. The term "image" used in this disclosure may refer to a 2D image, a 3D image, a 4D image, or any related image data (e.g., the PET data, projection data corresponding to the PET data). The image data may correspond to a distribution of PET tracers within the subject (e.g., a patient) or a coincidence distribution of the plurality of voxels within the subject represented in the form of, e.g., a sinogram. As used herein, a PET tracer may refer to a substance that may undergo certain changes under the influence of an activity or functionality within the subject, whose activity and/or functionality are to be visualized and/or studied. This is not intended to limit the scope the present disclosure. For persons having ordinary skills in the art, a certain amount of variations, changes, and/or modifications may be deducted under guidance of the present disclosure. Those variations, changes, and/or modifications do not depart from the scope of the present disclosure.

Figure 1A:
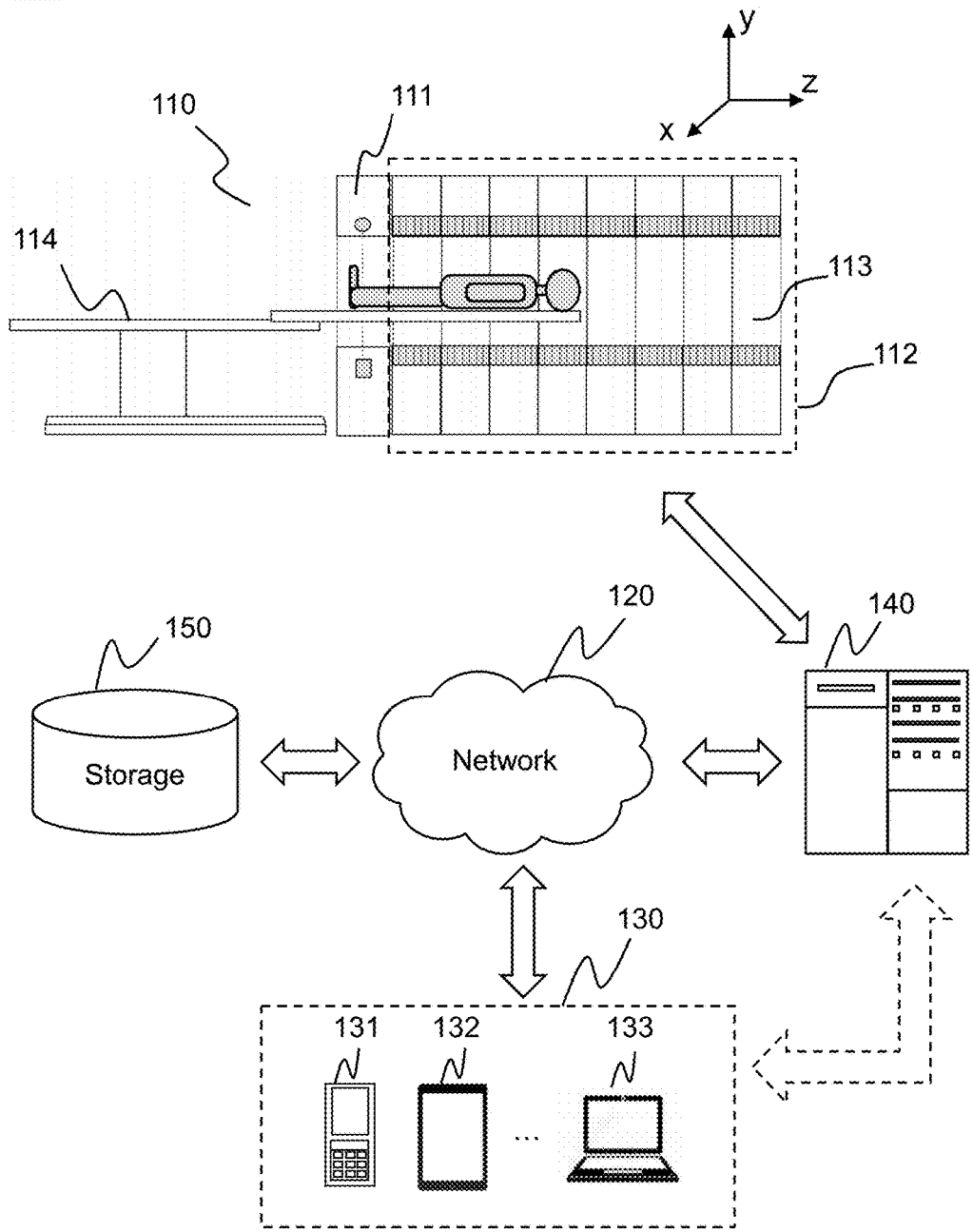
FIG. 1A is a schematic diagram illustrating an exemplary imaging system according to some embodiments of the present disclosure.

FIG. 1A is a schematic diagram illustrating an exemplary imaging system 100 according to some embodiments of the present disclosure. In some embodiments, the imaging system 100 may be a single-modality system or a multi-modality system. Exemplary multi-modality imaging system may include a computed tomography-positron emission tomography (CT-PET) system, a magnetic resonance-positron emission tomography (MR-PET) system, etc. In some embodiments, the imaging system 100 may include modules and/or components for performing imaging and/or related analysis. Merely by way of example, as illustrate in FIG. 1A, the imaging system 100 may include an imaging section 110, a network 120, one or more terminals 130, a processing engine 140, and storage 150; the imaging section 110 may include a PET scanner 112. The components in the imaging system 100 may be connected in one or more of various ways. Merely by way of example, the imaging section 110 may be connected to the processing engine 140 through the network 120. As another example, the imaging section 110 may be connected to the processing engine 140 directly as illustrated in FIG. 1A. As a further example, one or more of the terminal 130 may be connected to another component of the imaging system 100 (e.g., the processing engine 140) via the network 120 as illustrated in FIG. 1A. As still a further example, at least one terminal 130 may be connected to the processing engine 140 directly as illustrated by the dotted arrow in FIG. 1A. As still a further example, the storage 150 may be connected to another component of the imaging system 100 (e.g., the processing engine 140) directly as illustrated in FIG. 1A, or through the network 120.

The PET scanner 112 may include a detection region 113, a table 114, and one or more detector units. An individual detector unit may further include one or more detector subunits. The one or more detector subunits may include a plurality of PET detectors. Detailed descriptions about the PET detector, the detector subunit, and the detector unit may be found in FIG. 3A, FIG. 3B, and FIG. 3C, and descriptions thereof. The plurality of detectors may detect radiation events of photons emitted from the detection region 113. The table 114 may transport a scan object into and out of the detection region 113, and/or facilitate the positioning of the scan object in the detection region 113.

In some embodiments, a CT scanner 111 may be added to the imaging system 100 (e.g., as a part of the imaging section 110), and the imaging system may be a multi-modality imaging system. In some embodiments, the PET scanner 112 and CT scanner 111 may be installed separately on a gantry so that the PET scanner 112 does not interfere with the operation of the CT scanner 111. The CT scanner 111 may be a spiral CT, an electron beam CT, an energy spectrum CT, etc. In some embodiments, the spiral CT may be a multi-slice spiral CT or a multi-row spiral CT. For example, the spiral CT may be an 8 slices spiral CT scanner.

During an exemplary CT-PET scan, a scan object may be supported by the table 114 and moved into the detection region 113. CT detectors (not shown in the figure) may detect radiation events of X-rays in the detection region 113. After the CT scan, the scan object may then undergo a PET scan. After a reconstruction of a CT image based on data from the CT scan and a reconstruction of a PET image based on data from the PET scan, the multi-modality imaging system 100 may create a fused image that includes the PET image spatially registered to the CT image.

In some embodiments, the PET scan may be implemented by scanning one or more scan regions of the scan object. The one or more scan regions may be generated by dividing a volume of interest of the scan object into one or more parts. In some embodiments, the volume of interest of the scan object may be the entire volume of the scan object. In some embodiments, the volume of interest of the scan object may be a portion of the scan object. A scan region may correspond to a portion of a table on which the scan object is placed during the PET scan. By moving the table 114 into the detection region 113 along the z axis, each of the one or more scan regions may be scanned. PET data of respective scan regions may then be obtained. At least two scan regions of the one or more scan regions may at least partially overlap. In some embodiments, the one or more scan regions may completely cover the volume of interest the scan object. A PET sub-image may be generated based on PET data of a scan region. The PET image of the scan object may be obtained by stitching one or more PET sub-images of the one or more scan regions. The PET image of the scan object may also be directly obtained based on the entire PET data of the one or more scan regions.

As used in the present disclosure, the PET scanner may include a plurality of detector units, and each of the plurality of detector units may be span a certain width along the z axis. In some embodiments, a scan region may correspond to at least one detector unit. When a detector unit is determined as a non-functional (i.e., in an abnormal working status) detector unit, PET data relating to a scan region corresponding to the non-functional detector unit may be inaccurate. In some embodiments, the PET data relating to the scan region corresponding to the non-functional detector unit may be excluded from further processing. In some embodiments, the PET data relating to the scan region corresponding to the non-functional detector unit may be replaced by performing a re-scan of the scan region. For example, by moving the table 114 or the PET scanner 112 along the z axis, the scan region corresponding to the non-functional detector unit may be moved to a position that corresponds to a functional (i.e., in a normal working status) detector unit. The scan region may then be re-scanned when it is positioned corresponding to at least one functional detector unit. Accurate PET data relating to the scan region may be obtained, and may replace the PET data relating to the scan region obtained in the previous PET scan. The PET image of the scan object may be obtained based on PET data relating to the one or more scan regions that is collected by function detector units (or detector subunits).

The network 120 may include any suitable network that can facilitate exchange of information and/or data for the imaging system 100. In some embodiments, one or more components of the imaging section 110 (e.g., the CT scanner 111, the PET scanner 112, etc.), the terminal 130, the processing engine 140, the storage 150, etc., may communicate information and/or data with one or more other components of the imaging system 100 via the network 120. For example, the processing engine 140 may obtain data from the imaging section 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the multi-modality imaging system 110 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the PET scanner 112, the terminal 130, and/or the storage 150. In some embodiments, the processing engine 140 may be a computer, a user console, a single server or a server group, etc. The server group may be centralized or distributed. In some embodiments, the processing engine 140 may be local or remote. For example, the processing engine 140 may access information and/or data stored in the PET scanner 112, the terminal 130, and/or the storage 150 via the network 120. As another example, the processing engine 140 may be directly connected to the PET scanner 112, the terminal 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented on a computing device 200 having one or more components as illustrated in FIG. 2.

The storage 150 may store data, instructions, and/or any other information. In some embodiments, the storage 150 may store data obtained from the terminal 130 and/or the processing engine 140. In some embodiments, the storage 150 may store data and/or instructions that the processing engine 140 may execute or use to perform exemplary methods described in the present disclosure. In some embodiments, the storage 150 may include mass storage, removable storage, volatile read-and-write memory, read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the imaging system 100 (e.g., the processing engine 140, the terminal 130, etc.). One or more components in the imaging system 100 may access the data or instructions stored in the storage 150 via the network 120. In some embodiments, the storage 150 may be directly connected to or communicate with one or more other components in the imaging system 100 (e.g., the processing engine 140, the terminal 130, etc.). In some embodiments, the storage 150 may be part of the processing engine 140.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios. Merely by way of example, some other components may be added into the imaging system 100, such as a subject positioning module, a gradient amplifier module, and other devices or modules.

Figure 1B:
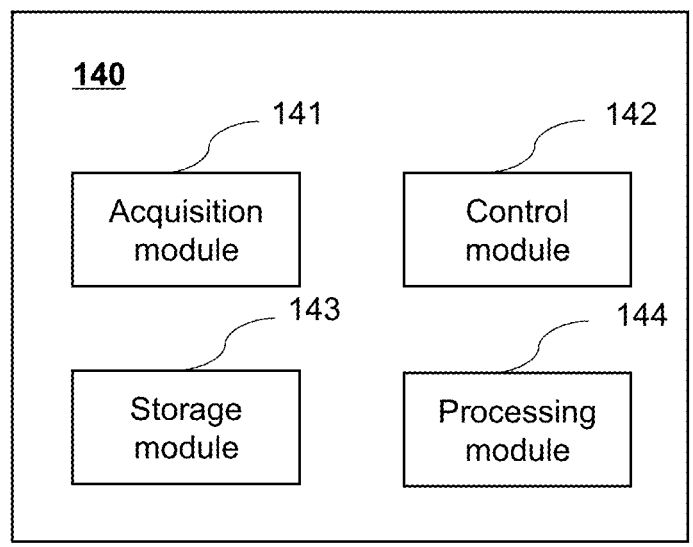
FIG. 1B is a block diagram illustrating a process engine according to some embodiments of the present disclosure.

FIG. 1B is a block diagram illustrating a processing engine according to some embodiments of the present disclosure. In some embodiments, the processing engine 140 may be implemented on a computing device 200 as illustrated in FIG. 2. As illustrated in FIG. 1B, the process engine 140 may include an acquisition module 141, a control module 142, a storage module 143, and a processing module 144.

The acquisition module 141 may acquire or receive CT data and/or PET data. Merely by way of example with reference to a PET scanner 112, the acquisition module 141 may acquire or receive PET data. In some embodiments, during a PET scan or analysis, PET tracer (also referred to as "PET tracer molecules") are first introduced into a scan object before an imaging process begins. During the PET scan, the PET tracer molecules may emit positrons, namely the antiparticles of electrons. A positron has the same mass as and the opposite electrical charge with respect to an electron, and it may undergo an annihilation (also referred to as an "annihilation event") with an electron (that may naturally exist in abundance within the scan object) as the two particles collide. An electron-positron annihilation may result in two 511 keV gamma photons, which, upon their own generation, begin to travel in (substantially) opposite directions with respect to one another. This property of collinearity of the two gamma photons may be used to define a line-of-sight of the event without the need for physical collimation. The line connecting the two gamma photons may be referred to as a "line of response (LOR)." The acquisition module 141 may obtain trajectory and/or information of gamma photons (also referred to as the "PET data"). The PET data may include a list of single events, coincident events, annihilation events, transverse and longitudinal positions of LORs, or the like, or a combination thereof. The PET data may be used to determine the distribution of the PET tracer molecules in the image domain and/or the coincidence distribution of voxels in the sinogram coordinate system. In some embodiments, the acquisition module 141 may include different zones to acquire PET data collected by a plurality of detector units, respectively.

In some embodiments, the PET tracer may include carbon (11C), nitrogen (13N), oxygen (15O), fluorine (18F), or the like, or a combination thereof. In some embodiments, for a single photon emission computed tomography (SPECT) system, a SPECT tracer may be introduced into a scan object. The SPECT tracer may include technetium-99m, iodine-123, indium-111, iodine-131, or the like, or a combination thereof. Accordingly, in some embodiments, the PET tracer or SPECT tracer of the present disclosure may be organic compounds containing one or more of such isotopes. These tracers are either similar to naturally occurring substances or otherwise capable of interacting with the functionality or activity of interest within the scan object. Hence, distributional information of the tracer may be used as an indicator of the scan object functionality.

The control module 142 may generate a control parameter for controlling the acquisition module 141, the storage module 143, and/or the processing module 144. For example, the control module 142 may control the acquisition module 141 as to whether to acquire PET data, acquire PET data corresponding to the PET scanner 112/a detector unit of the PET scanner 112/a detector subunit of a detector unit, or the time when PET data acquisition may occur. As another example, the control module 142 may control processing module 144 to generate reconstruction data and select different algorithms to process the reconstruction data for image reconstruction. In some embodiments, the control module 142 may receive a real-time or a predetermined command provided by a user (e.g., a doctor) and adjust the acquisition module 141, and/or the processing module 144 to take images of a scan object according to the received command. In some embodiments, control module 142 may communicate with other modules in the imaging system 100 for exchanging information or data.

The storage module 143 may store the acquired PET data, or the control parameters, or the like, or a combination thereof. In some embodiments, the storage module 143 may include mass storage, removable storage, volatile read-and-write memory, read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage module 143 may store one or more programs and/or instructions that may be executed by one or more processors of the imaging system 100 (e.g., processing module 144) to perform exemplary methods described in this disclosure. For example, storage module 143 may store program(s) and/or instruction(s) executed by the processor(s) of the imaging system 100 to acquire PET data, or reconstruct an image based on the PET data.

The processing module 144 may process data and/or information received from modules in the imaging system 100. In some embodiments, the processing module 144 may process PET data acquired by the acquisition module 141, or retrieved from storage module 143. In some embodiments, the processing module 144 may reconstruct a PET image based on the PET data, generate reports including one or more PET images and/or other related information, or the like. For example, processing module 144 may process the PET data based on a gating approach and reconstruct a PET image based on the gated PET data.

It should be noted that the above description of the processing engine 140 is merely provided for the purposes of illustration, and not intended to limit the scope of the present disclosure. In some embodiments, one or more modules illustrated in FIG. 1B may be implemented in at least part of the exemplary imaging system 100 illustrated in FIG. 1A. For example, at least two modules of the acquisition module 141, the control module 142, the storage module 143, and/or the processing module 144 may be integrated into a console. Via the console, a user may set parameters for scanning, control the imaging procedure, control a parameter of the reconstruction of an image, view the reconstructed images, etc. In some embodiments, the console may be implemented via a host computer.

FIG. 2 is a block diagram illustrating exemplary hardware and software components of computing device 200 on which the imaging system 100 may be implemented according to some embodiments of the present disclosure. In some embodiments, the computing device 200 may include a processor 202, a memory 204, and a communication port 206.

The processor 202 may execute computer instructions (program code) and perform functions of the processing module 144 in accordance with techniques described herein. Computer instructions may include routines, programs, objects, components, data structures, procedures, modules, and functions, which perform particular functions described herein. For example, the processor 202 may process the data or information received from the acquisition module 141, the control module 142, the storage module 143, or any other component of imaging system 100. In some embodiments, the processor 202 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof. For example, processor 202 may include a microcontroller to process the PET data from the PET scanner 112 for image reconstruction.

The memory 204 may store the data or information received from the acquisition module 141, the control module 142, the storage module 143, the processing module 144, or any other component of imaging system 100. In some embodiments, the memory 204 may include mass storage, removable storage, volatile read-and-write memory, read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the memory 204 may store one or more programs and/or instructions to perform exemplary methods described in the present disclosure. For example, the memory 204 may store a program for the processing module 144 for reconstructing a PET image based on the PET data acquired by the PET scanner 112 and/or the acquisition module 141.

The communication port 206 may transmit to and receive information or data from any one of the acquisition module 141, the control module 142, the storage module 143, and the processing module 144. In some embodiments, the communication port 206 may include a wired port (e.g., a Universal Serial Bus (USB) port, a High Definition Multi-media Interface (HDMI) port, or the like) or a wireless port (a Bluetooth port, an infrared interface, a WiFi port, or the like).

Merely for illustration, only one processor (the processor 202) is described in the computing device 200. However, it should be noted that the computing device 200 in the present disclosure may also include multiple processors, thus operations and/or method steps that are performed by one processor as described in the present disclosure may also be jointly or separately performed by the multiple processors. For persons having ordinary skills in the art, multiple variations and modifications may be made under the teaching of the present invention. However, those variations and modifications do not depart from the scope of the present disclosure.

Figure 3A:
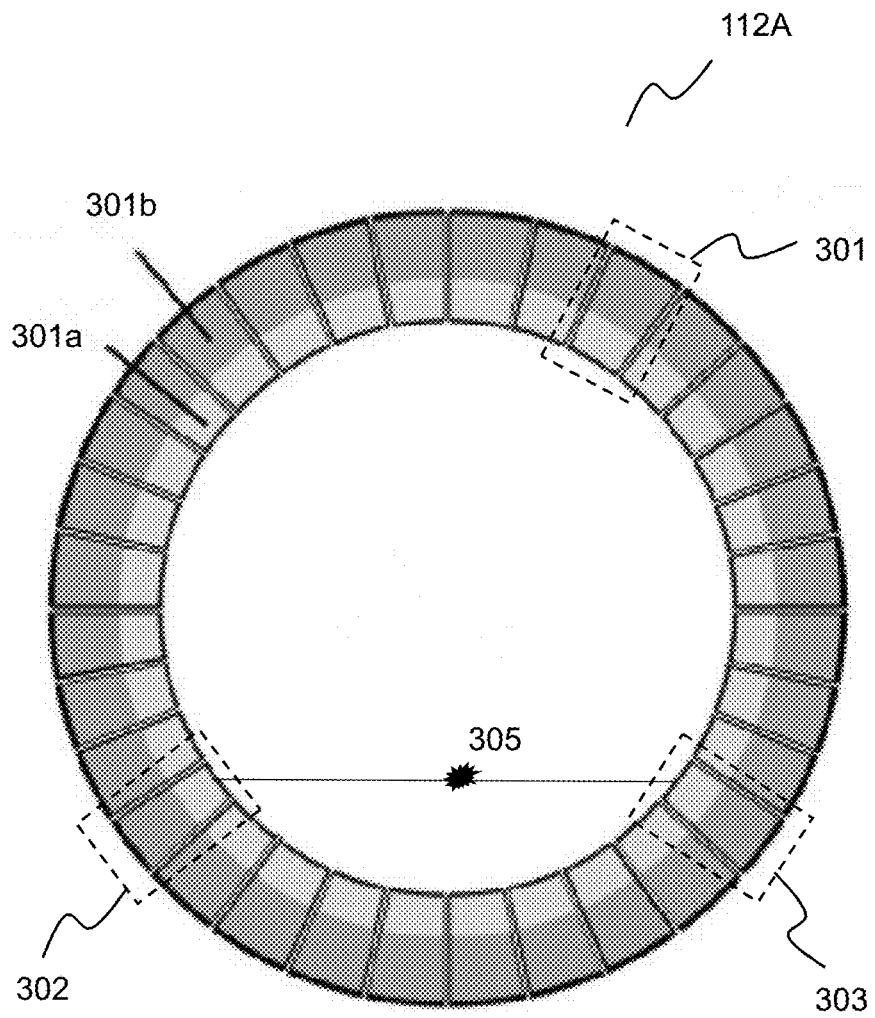
FIG. 3A is a schematic diagram illustrating a detector subunit according to some embodiments of the present disclosure.

FIG. 3A is a schematic diagram illustrating a detector subunit according to some embodiments of the present disclosure. In some embodiments, a detector subunit 112A may include a plurality of PET detectors (e.g., a PET detector 301, a PET detector 302, a PET detector 303, etc.) and detection circuits (not shown in the figure). The PET detectors may further include a plurality of crystal elements (e.g., a crystal element 301a) and/or photomultiplier tubes (e.g., a photomultiplier tube 301b). In some embodiments, a crystal element may correspond to a photomultiplier tube. The crystal element may emit visible light photons after an interaction with photons from radiation events originating from a scan object. The corresponding photomultiplier tube may amplify and convert optical signals of the visible light photons into electrical signals. The electrical signals may then be transmitted to detection circuits for subsequent processing. In some embodiments, a photomultiplier tube applicable in the present disclosure may be a single-channel photomultiplier tube or a multi-channel photomultiplier tube. In some embodiments, the plurality of PET detectors may be arranged in a ring-shaped pattern, and an area surrounded by the PET detectors may provide a detection region of the detector subunit 112A.

During a PET scan or analysis, a positron undergoes an annihilation event 305 with an electron as the two particles collide. The annihilation event 305 may result in two photons (e.g., gamma photons), and the two photons may begin to travel at (substantially) opposite directions. One of the two photons may be counted by the PET detector 302, and the other one may be counted by the PET detector 303. A single photon counted by a detector may be referred to as a "single event." The line connecting the two photons may be an LOR, and one or more annihilation events may occur on the LOR. In some embodiments, PET data collected by a detector subunit as used in the present disclosure may include trajectory and/or information of photons detected by all detectors in the detector subunit.

In some embodiments, multiple single events detected by the PET detector in the detector subunit 112A may further be converted into one or more coincident events. A coincident event may refer to two single events counted by two PET detectors respectively within a coincident time window (e.g., less than 10 ns, etc.) A coincident event may constitute two single events counted by the same detector subunit of a detector unit. A coincident event may constitute two single events counted by the different detector subunits of the same detector unit. A coincident event may constitute two single events counted by the different detector subunits of different detector units. In some embodiments, a coincident event may correspond to scattering coincidence, random coincidence, or true coincidence. A scattered coincidence may be one in which at least one of the counted single event has undergone at least one Compton scattering event before counted by a PET detector. A random coincidence may occur when two photons arising from different annihilation events within the coincident time window. A true coincidence event may include two single events in which photons derive from a single positron—electron annihilation counted by two detectors within the coincident time window. In some embodiment, the true coincidence event may be determined by the coincidence detection including detector sensitivity correction (normalization), isotope time decay correction, dead time correction, random coincidence correction, scattering coincidence correction, attenuation correction, geometric correction, or the like, or a combination thereof.

Figure 3B:
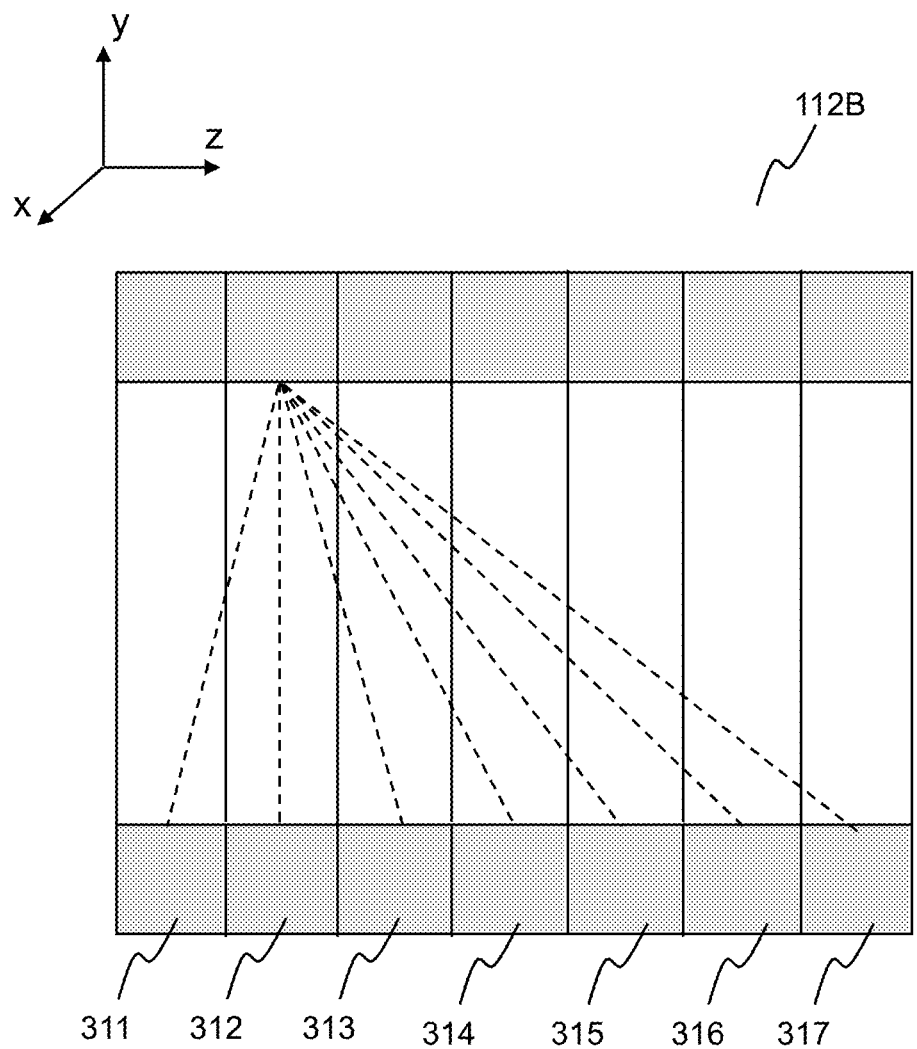
FIG. 3B is a schematic diagram illustrating a detector unit according to some embodiments of the present disclosure.

FIG. 3B is a schematic diagram illustrating a detector unit according to some embodiments of the present disclosure. The detector unit 112B may include a detector subunit 311, a detector subunit 312, a detector subunit 313, a detector subunit 314, a detector subunit 315, a detector subunit 316, and a detector subunit 317. In some embodiments, the detector subunits of the detector unit 112B may be arranged in a row along the z axis. An opening area formed by the detector subunits may constitute a detection region of the detector unit 112B. A scan object may be moved into and out of the detection region of a detector unit along the z axis. The detector unit 112B illustrated in FIG. 3B may be formed by combining 7 ring-shaped detector subunits. A ring-shaped detector subunit may be also referred to as a detector ring. It should be noted that the above description of the PET unit is merely provided for the purposes of illustration, more detector subunits (e.g., detector rings) may be added to the PET unit.

In some embodiments, during a PET scan or analysis, a plurality of annihilation photons may be counted by detectors of detector subunits of the detector unit 112B. The detector unit 112B may then generate PET data based on a plurality of single events corresponding to the plurality of annihilation photons.

Figure 3C:
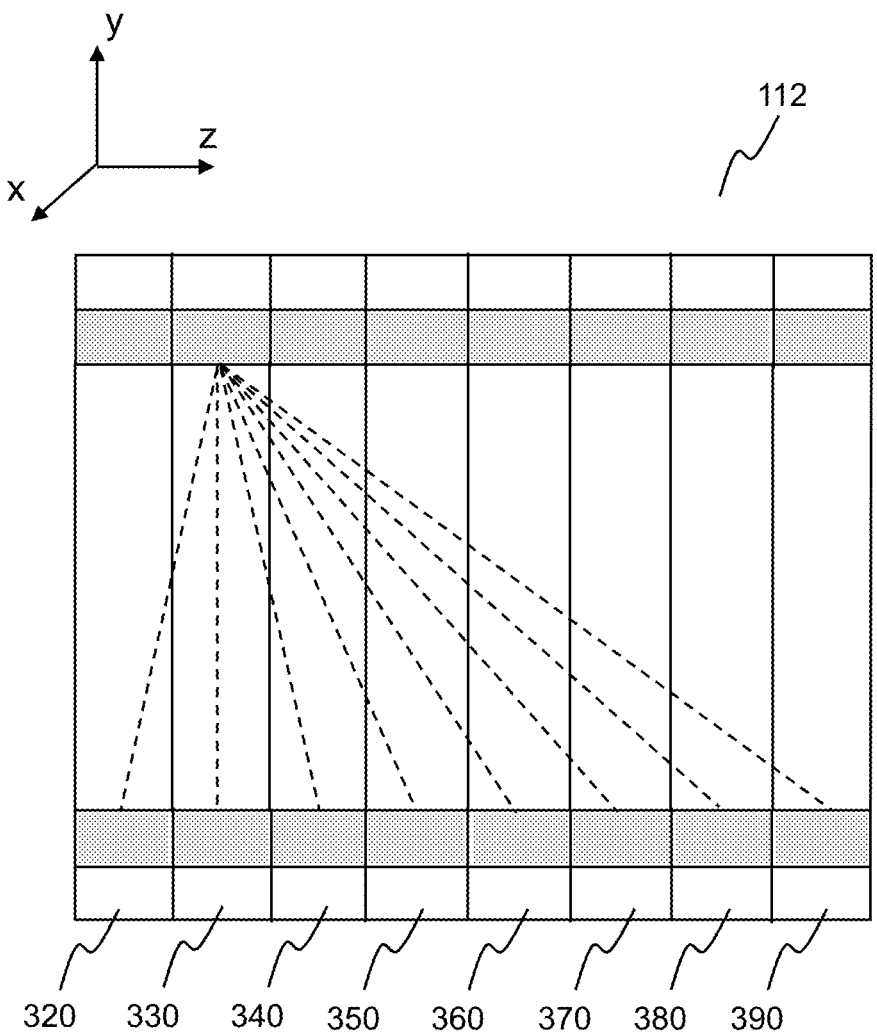
FIG. 3C is a schematic diagram illustrating a PET scanner according to some embodiments of the present disclosure.

FIG. 3C is a schematic diagram illustrating a PET scanner according to some embodiments of the present disclosure. The PET scanner 112 may include a detector unit 320, a detector unit 330, a detector unit 340, a detector unit 350, a detector unit 360, a detector unit 370, a detector unit 380, and a detector unit 390. A detector unit may include a plurality of detector subunits, as exemplified in FIG. 3B and the description thereof. In some embodiments, the plurality of detector units of the PET scanner 112 may be arranged in a row along the z axis. An opening area formed by the detector units may constitute a detection region of the PET scanner 112. A scan object may be moved into and out of the detection region of a PET scanner along the z axis. It should be noted that the above description of the PET scanner is merely provided for the purposes of illustration, more detector units may be added to the PET scanner.

In some embodiments, the plurality of detector units of the PET scanner 112 may have a respective position label. A position label may represent a position of a detector unit, relative to other detector units, in the PET scanner 112. An order of the plurality of detector units arranged in the PET scanner 112 may be determined based on the respective position labels of the plurality of detector units. The PET scanner 112 illustrated in FIG. 3C may be formed by combining 8 detector units that are arranged along the z axis. The position labels of the eight detector units may be set as U1, U2, U3, U4, U5, U6, U7, and U8, respectively, according to where a detector unit is arranged, relative to the other detector units, in the PET scanner 112. Position label U1 may correspond to the detector unit 320. Position label U2 may correspond to the detector unit 330. Position label U3 may correspond to the detector unit 340. Position label U4 may correspond to the detector unit 350. Position label U5 may correspond to the detector unit 360. Position label U6 may correspond to the detector unit 370. Position label U7 may correspond to the detector unit 380. Position label U8 may correspond to the detector unit 390.

In some embodiments, during a PET scan or analysis, a plurality of annihilation gamma photons may be counted by detectors of the detector units of the PET scanner 112. The PET scanner 112 may then generate PET data based on a plurality of single events corresponding to the plurality of annihilation gamma photons. In some embodiments, PET data collected by the PET scanner 112 (also referred to as "the entire PET data") as used in the present disclosure may include data of multiple single events detected by all detector units in the PET scanner. In some embodiments, the entire PET data or some of the entire PET data may be used to determine a distribution of the PET tracer molecules in the image domain and/or the coincidence distribution of voxels in the sinogram coordinate system.

Any two detector units corresponding to a coincident event may be referred to as a "detector unit pair." A detector unit pair may count one or more coincident events. In the present disclosure, a detector unit pair may be denoted by the position labels of the detector units. For example, a coincidence event may be counted by a PET detector located in the detector unit 330 with position label U2 and a PET detector located in the detector unit 340 with position label U3, and the combination of detector unit 330 and detector unit 340 may be referred as a detector unit pair. As another example, a coincidence event may be counted by PET detectors both located in the detector unit 330 alone, and the combination of detector unit 330 and detector unit 330 may be referred as a detector unit pair. A unit difference may represent a position difference between the two detector units in a detector unit pair. For example, the unit difference of a detector unit pair including detector unit 330 and detector unit 350 may be two according to the position labels. As another example, the unit difference of a detector unit pair including detector unit 330 alone may be zero. The unit difference may also represent an axial distance between the two detector units of a detector unit pair. For example, the unit difference of the detector unit pair including detector unit 330 and detector unit 350 may be a distance from the center of detector unit 330 to the center of detector unit 350. In some embodiments, the PET data used in image reconstruction may be part of the acquired PET data. A PET data selection may be performed according to a rule. For instance, if the unit difference of a detector unit pair exceeds a threshold, a coincidence event counted by the detector unit pair may be not used in image reconstruction due to factors including, for example, traveling attenuation of the photons.

It should be noted that the above description of the detector, detector subunit, and detector unit is merely provided for the purposes of illustration, and not intended to limit the scope of the present disclosure. For persons having ordinary skills in the art, multiple variations and modifications may be made under the teachings of the present disclosure. For example, more detectors may be added to a detector subunit, and detectors of a detector subunit may be implemented in any suitable manner, e.g., a ring, a rectangle, or an array. As another example, more detector subunits may be added to a detector unit, and an opening area formed by detector subunits may constitute a detection region of a detector unit. As a further example, more detector units may be added to a PET scanner, and a chance of single events to be counted may increase.

Figure 4:
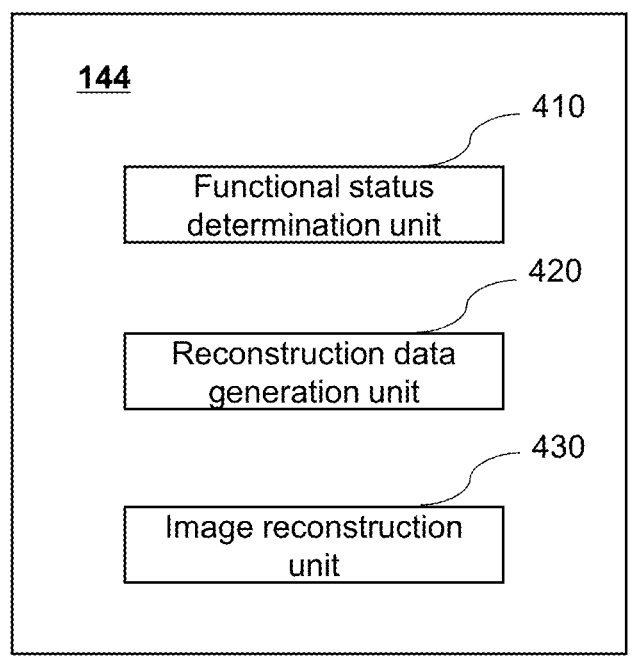
FIG. 4 is a block diagram of an exemplary processing module according to some embodiments of the present disclosure.

FIG. 4 is a block diagram of an exemplary processing module according to some embodiments of the present disclosure. The processing module 144 may include a functional status determination unit 410, a reconstruction data generation unit 420, and an image reconstruction unit 430. In some embodiments, the units may be connected with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or a combination thereof).

The functional status determination unit 410 may determine functional status of a detector unit of the PET scanner 112. In some embodiments, the functional status of a detector unit may be assessed based on one or more performance parameters via the functional status determination unit 410. The functional status determination unit 410 may generate a performance parameter of a detector unit in the PET scanner 112 real-time. Exemplary performance parameters of a detector unit may include a counting rate. As used herein, a counting rate may be equal to the number (or counts) of single events counted by the detector unit per unit time, e.g., one second. The counting rate for a detector unit may be determined by dividing the counts of single events counted by the detector unit in a certain time period (e.g., 10 seconds) by the certain time period. For example, a counting rate of a detector unit obtained real-time may be determined by or transmitted to the functional status determination unit 410, and may be compared with a threshold by the functional status determination unit 410. In some embodiments, when a counting rate of a detector unit is below a threshold, the functional status determination unit 410 may designate the detector unit as defective or non-functional, indicating that the detector unit is under a negative status (e.g., abnormal working status). When a counting rate of a detector unit equals or exceeds a threshold, the functional status determination unit 410 may designate the detector unit functional, indicating that the detector unit is under a positive status (e.g., normal working status).

In some embodiments, the functional status determination unit 410 may determine functional status of a detector unit based on a functional status of a detector subunit. The functional status determination unit 410 may determine the functional status of a detector subunit based on the counting rate of a detector subunit. The counting rate for a detector subunit may be determined by dividing the counts of single events counted by the detector subunit in a certain time period (e.g., 10 seconds) by the certain time period. When a counting rate of a detector subunit is below a threshold, the functional status determination unit 410 may designate the detector subunit as defective or non-functional, indicating that the detector unit including the defective detector subunit is in a negative status (e.g., abnormal working status).

In some embodiments, the functional status determination unit 410 may determine the functional status of a detector subunit of a detector unit based on the performance parameter. In some embodiments, if a detector subunit of a detector unit is determined to be under a negative status, the detector unit including the non-functional detector subunit may be designated as a non-functional unit.

The reconstruction data generation unit 420 may determine reconstruction data based on the current functional status of respective detector units and the PET data acquired by the corresponding detector units. The reconstruction data may be used to perform PET image reconstruction. The current functional status of a detector unit may be determined by the functional status determination unit 410. The PET data collected by the respective detector units may be obtained by the acquisition module 141. In some embodiments, the reconstruction data generation unit 420 may determine reconstruction data based on the PET data collected by a plurality of detector units according to the current functional status of the respective detector units. When there is no non-functional detector unit in the PET scanner, the acquisition module 141 may be set to a full data collection mode, and detector units (detector subunits) may operate in a full operation mode. Under the full data collection mode, the acquisition module 141 may collect PET data detected by all detector units. Under the full operation mode, all detector units (or all detector subunits) in the PET scanner may be allowed to operate. The reconstruction data generation unit 420 may determine the reconstruction data based on the PET data of all detector units acquired by the acquisition module 141.

When the functional status determination unit 410 determines that there is a non-functional detector unit or a non-functional detector subunit in the PET scanner before or during a PET scan, a data collection mode for generating reconstruction data may be selected. In some embodiments, the acquisition module 141 may be set to a partial data collection mode while detector units (detector subunits) are allowed to maintain at the full operation mode. Under the partial data collection mode, only a portion of the collected PET data may be used for further processing. For instance, PET data collected by the non-functional detector unit or non-functional detector subunit may be excluded, and PET data collected by a functional detector unit or functional detector subunit may be preserved for further processing. Under the full operation mode, all detector units (or all detector subunits) in the PET scanner, including the functional ones and the non-functional ones, may be allowed to operate. The reconstruction data generation unit 420 may generate the reconstruction data for performing PET image reconstruction based on the preserved PET data collected by the functional detector unit(s) or functional detector subunit(s).

In some embodiments, the acquisition module 141 may be set to a full data collection mode, and detector units (detector subunits) may operate in a partial operation mode. Under the partial operation mode, non-functional detector unit(s) may be shut down by, e.g., the control module 142, while a detector unit including a non-functional detector subunit is designated as a non-functional detector unit. Under the full data collection mode, all collected PET data may be used for further processing. For instance, the PET scanner is set to a partial operation mode in which all non-functional detector unit(s) are shut down, and only the functional detector units are allowed to operation, PET data collected by all functional detector unit(s) may be obtained and preserved for further processing. The reconstruction data generation unit 420 may generate the reconstruction data based on all PET data of functional detector unit(s) acquired by the acquisition module 141, each of which does not include a non-functional detector subunit.

When one or more non-functional detector units are identified in the PET scanner, the reconstruction data may be determined based on PET data collected by the functional detector units. In some embodiments, the reconstruction data may include PET data collected by functional detector units in a subgroup that are located together and not separated by a non-functional detector unit. In some embodiments, if there are more than one subgroups containing functional detector unit(s) that are located together and not separated by a non-functional detector unit, the reconstruction data may include PET data collected by the subgroup including more functional detector units.

In some embodiments, when the number of detector units in the subgroup that includes more functional detector units is below a threshold, an operation of data compensation may be performed. The data compensation may be performed mathematically according to an algorithm. Exemplary algorithms may include a closest element algorithm, a bilinear interpolation algorithm, a cubic interpolation algorithm, etc. In some embodiments, the data compensation may also be implemented by performing another PET scan as directed by, e.g., the control module 142. More descriptions may be found in FIG. 7A and FIG. 7B, and descriptions thereof.

The image reconstruction unit 430 may reconstruct a PET image based on the reconstruction data. The reconstruction data may be generated by the reconstruction data generation unit 420. In some embodiments, the image reconstruction unit 430 may employ different kinds of imaging reconstruction techniques for image reconstruction. Exemplary image reconstruction techniques may include Fourier reconstruction, constrained image reconstruction, regularized image reconstruction, or the like, or a variation thereof, or a combination thereof. In some embodiments, the image reconstruction unit 430 may use different reconstruction algorithms including an analytic reconstruction algorithm or an iterative reconstruction algorithm for image reconstruction. Exemplary analytic reconstruction algorithms may include a filter back projection (FBP) algorithm, a back projection filter (BFP) algorithm, a p-filtered layer gram, or the like, or a combination thereof. Exemplary iterative reconstruction algorithms may include a Maximum Likelihood Expectation Maximization (ML-EM), an Ordered Subset Expectation Maximization (OSEM), a Row-Action Maximum Likelihood Algorithm (RAMLA), a Dynamic Row-Action Maximum Likelihood Algorithm (DRAMA), or the like, or a combination thereof.

In some embodiments, when a CT-PET multi-modality system is used, the image reconstruction unit 430 may reconstruct a CT image based on CT scanning data to display the shape and/or position of a scan object. Furthermore, the CT scanning data or the CT image may be used for attenuation correction of a PET or SPET scan. In some embodiments, when a PET scan is implemented by scanning one or more scan regions of the scan object, the image reconstruction unit 430 may include stitching PET subimages of the one or more scan regions of the scan object to generate a PET image of the scan object.

It should be noted that the above description of the processing module 144 is merely provided for the purposes of illustration, and not intended to limit the scope of the present disclosure. For persons having ordinary skills in the art, multiple variations and modifications may be made under the teachings of the present disclosure. For instance, the assembly and/or function of the processing module 144 may be varied or changed according to specific implementation scenarios. Merely by way of example, some other components may be added into the processing module 144, such as a position label setting unit, an image/data output unit, and other units.

Figure 5:
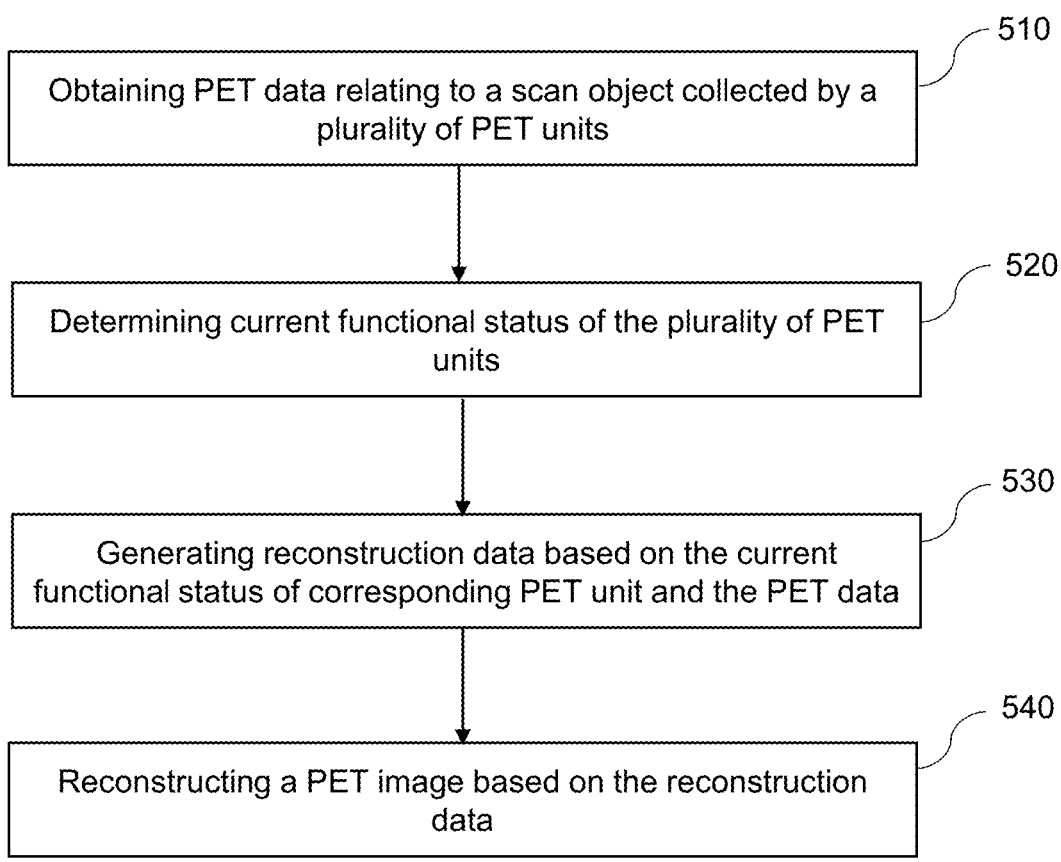
FIG. 5 is a flowchart illustrating an exemplary process of reconstructing a PET image according to some embodiments of the present disclosure.

FIG. 5 is a flowchart illustrating an exemplary process 500 of reconstructing a PET image according to some embodiments of the present disclosure. In some embodiments, one or more operations of the process 500 illustrated in FIG. 5 for PET image reconstruction may be implemented in the imaging system 100 illustrated in FIG. 1A. For example, the process 500 illustrated in FIG. 5 may be stored in the storage 150 in the form of instructions, and invoked and/or executed by the processing engine 140 (e.g., the processor of a computing device). As another example, a portion of the process 500 may be implemented on the PET scanner 112.

In 510, PET data relating to a scan object collected by a plurality of detector units may be obtained. The PET data relating to a scan object collected by a plurality of detector units may be obtained via the acquisition module 141. In some embodiments, PET data relating to a scan object collected by a plurality of detector units may be obtained from the storage module 143. The PET data collected by a plurality of detector units may further be used to determine the distribution of the PET tracer molecules in the image domain and/or the coincidence distribution of voxels in the sinogram coordinate system. The PET data may include one or more coincidence events counted by one or more detector unit pairs.

In 520, the current functional status of each of the plurality of detector units may be determined. The current functional status of the plurality of detector units may be determined by the functional status determination unit 410. In some embodiments, the functional status determination unit 410 may determine the current functional status of the plurality of detector units based on one or more performance parameters. The functional status determination unit 410 may generate one or more performance parameters of the detector units in the PET scanner 112 real-time. Exemplary performance parameters of a detector unit may include a counting rate. The counting rate for a detector unit may be determined by dividing the counts of single events counted by the detector unit in a certain time period by the certain time period. For example, a counting rate of a detector unit obtained real-time may be determined by or transmitted to the functional status determination unit 410, and may be compared with a threshold by the functional status determination unit 410. In some embodiments, when a counting rate of a detector unit is below a threshold, the detector unit may be designated as a non-functional unit by the functional status determination unit 410, indicating that the detector unit is under a negative status (e.g., abnormal working status). When a counting rate of a detector unit equals or exceeds a threshold, the detector unit may be designated as a functional unit by the functional status determination unit 410, indicating that the detector unit is under a positive status (e.g., normal working status).

In 530, reconstruction data may be determined based on the current functional status of respective detector units and the PET data acquired by the corresponding detector units. The reconstruction data may be used to perform PET image reconstruction. The current functional status of corresponding detector unit may be determined by the functional status determination unit 410. The PET data collected by the respective detector units may be obtained by the acquisition module 141. In some embodiments, PET data collected by a non-functional detector unit or detector subunit may be removed and not used to perform image reconstruction. In some embodiments, the reconstruction data generation unit 420 may determine reconstruction data based on the PET data collected by a plurality of detector units according to the current functional status of the respective detector units. The reconstruction data may include the PET data acquired by the functional detector units, each of which does not include a non-functional detector subunit.

In 540, a PET image may be reconstructed based on the reconstruction data. Image reconstruction of the PET image may be implemented by the image reconstruction unit 430. The reconstruction data may be determined by the reconstruction data generation unit 420. In some embodiments, any one of different kinds of imaging reconstruction techniques for image reconstruction may be used to reconstruct a PET image. Exemplary image reconstruction techniques may include Fourier reconstruction, constrained image reconstruction, regularized image reconstruction in parallel MRI, or the like, or a variation thereof, or a combination thereof. In some embodiments, different reconstruction algorithms including an analytic reconstruction algorithm or an iterative reconstruction algorithm for image reconstruction may be used. Exemplary analytic reconstruction algorithms may include a filter back projection (FBP) algorithm, a back projection filter (BFP) algorithm, a p-filtered layer gram, or the like, or a combination thereof. Exemplary iterative reconstruction algorithms may include a Maximum Likelihood Expectation Maximization (ML-EM), an Ordered Subset Expectation Maximization (OSEM), a Row-Action Maximum Likelihood Algorithm (RAMLA), a Dynamic Row-Action Maximum Likelihood Algorithm (DRAMA), or the like, or a combination thereof.

It should be noted that the above description of the process of reconstructing a PET image is merely provided for the purposes of illustration, and not intended to limit the scope of the present disclosure. For persons having ordinary skills in the art, multiple variations and modifications may be made under the teachings of the present disclosure. For example, process 500 may further include an operation of storing the PET data relating to a scan object collected by a plurality of detector units in the storage 150. As another example, process 500 may further include an operation of outputting the PET image. Such variations and modifications do not depart from the scope of the present disclosure.

Figure 6:
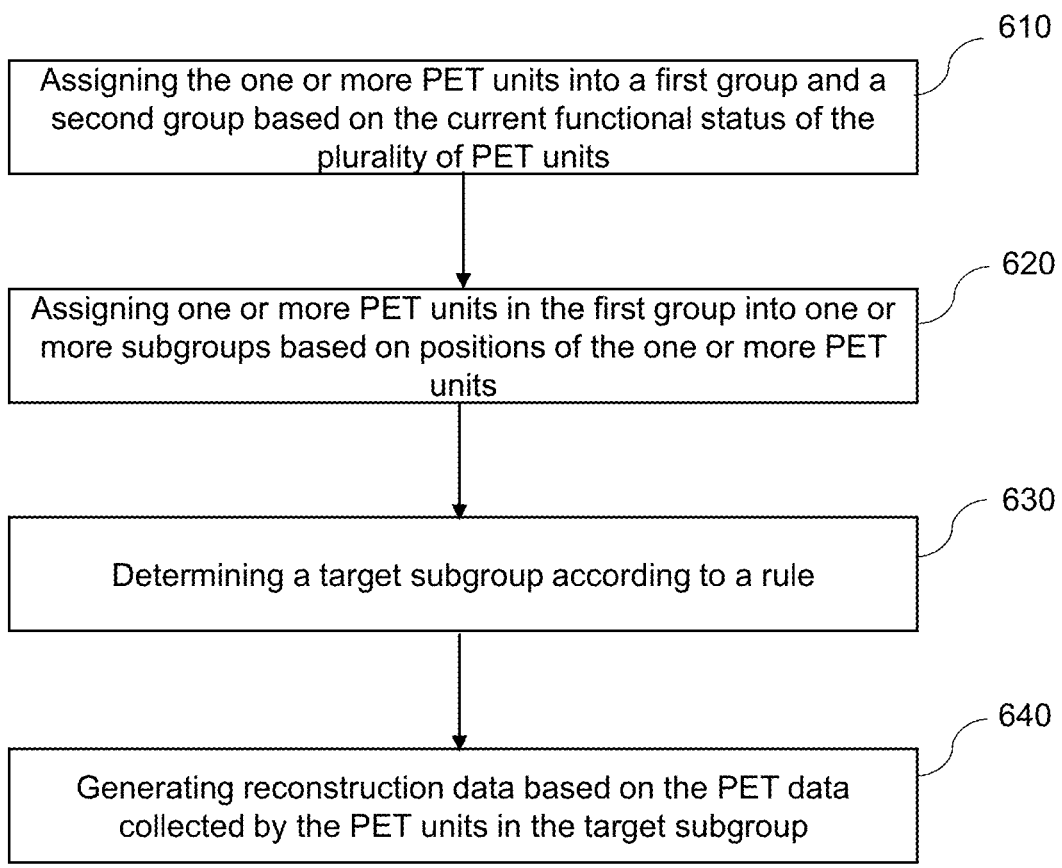
FIG. 6 is a flowchart illustrating an exemplary process of determining reconstruction data according to some embodiments of the present disclosure.

FIG. 6 is a flowchart illustrating an exemplary process of determining reconstruction data according to some embodiments of the present disclosure. In some embodiments, one or more operations of the process 600 illustrated in FIG. 6 for determining reconstruction data may be implemented in the imaging system 100 illustrated in FIG. 1A. For example, the process 600 illustrated in FIG. 6 may be stored in the storage 150 in the form of instructions, and invoked and/or executed by the processing engine 140 (e.g., the processor of a computing device).

In 610, the reconstruction data generation unit 420 may assign one or more detector units into different groups based on functional status of the one or more detector units. The reconstruction data generation unit 420 may assign one or more functional units into a first group and one or more non-functional detector unit into a second group. In some embodiments, the reconstruction data generation unit 420 may determine reconstruction data based on coincidence events counted by the detector unit(s) in the first group. In some embodiments, the first group may include one or more subgroups containing functional detector unit(s).

In 620, the reconstruction data generation unit 420 may further assign one or more functional detector units into different subgroups based on positions of the one or more detector units in the first group. The reconstruction data generation unit 420 may assign one or more detector unit(s) that are located together and not spatially separated by a non-functional detector unit into a subgroup. Two subgroups of functional detector units may be separated by one or more non-functional detector unit. In some embodiments, if a functional detector unit A is not adjacent to any other functional detector unit in the first group, the reconstruction data generation unit 420 may assign the functional detector unit A into a subgroup only containing the functional detector unit A.

In 630, the reconstruction data generation unit 420 may determine a target subgroup based on a rule. The rule may include comparing detector unit number of the one or more subgroups, and determine a subgroup as the target subgroup based on unit number of the different subgroups. In some embodiments, the reconstruction data generation unit 420 may determine reconstruction data based on coincidence events counted by the detector unit(s) of a subgroup that includes the most functional detector units than any other subgroup(s) in the first group.

In 640, the reconstruction data generation unit 420 may determine reconstruction data based on the PET data collected by the detector unit(s) in the target subgroup. PET data may include single events counted by the detector unit(s) in the target subgroup. The reconstruction data may be determined based on coincidence events counted by one or more detector unit pairs. The reconstruction data generation unit 420 may generate reconstruction data based on coincidence events counted by one or more detector unit pairs belonging to detector unit(s) in the target subgroup.

It should be noted that the above description of the process of determining reconstruction data is merely provided for the purposes of illustration, and not intended to limit the scope of the present disclosure. For persons having ordinary skills in the art, multiple variations and modifications may be made under the teachings of the present disclosure. For example, process 600 may further include an operation in which the functional status of respective detector units may be recorded by the computing device 200. As another example, process 600 may further include an operation in which the PET scanner 112 may be shut down when the unit number of the target subgroup is below a threshold, e.g., 2. Such variations and modifications do not depart from the scope of the present disclosure.

Figures 7A, 7B:
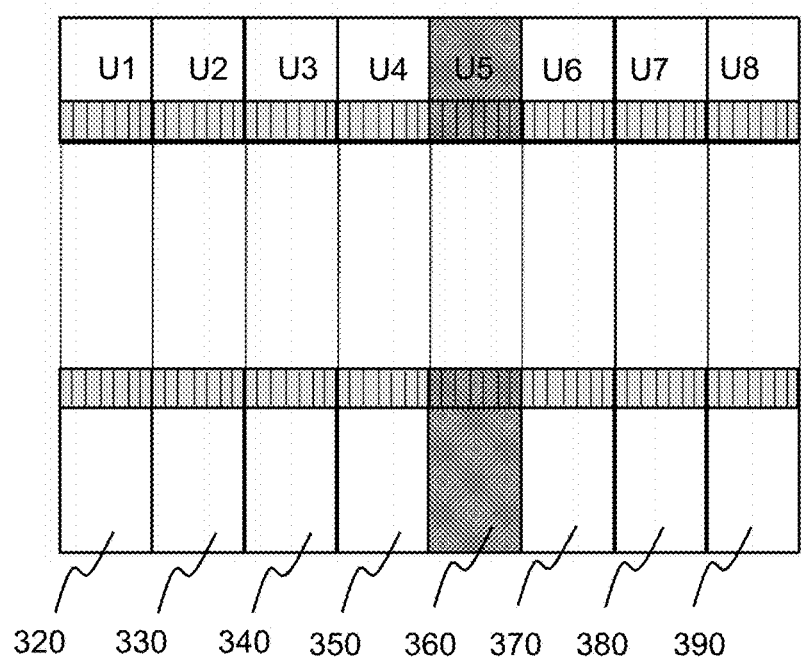
FIG. 7A is a schematic diagram illustrating a PET scanner with a non-functional detector unit.
FIG. 7B is an exemplary illustration of coincident events of the PET scanner illustrated in FIG. 7A.

FIG. 7A illustrates an exemplary PET scanner with a non-functional detector unit. As shown in FIG. 7A, the PET scanner 112 may include detector unit 320 labeled as U1, detector unit 330 labeled as U2, detector unit 340 labeled as U3, detector unit 350 labeled as U4, detector unit 360 labeled as U5, detector unit 370 labeled as U6, detector unit 380 labeled as U7, and detector unit 390 labeled as U8. FIG. 7B illustrates a map of detector unit pairs that detect coincident events. For example, C (1, 1) may represent one or more coincidence events counted by detector unit 320 and detector unit 320, and C (1, 2) may represent one or more coincidence events counted by detector unit 320 and detector unit 330, and so on. As shown in FIG. 7A, detector unit 360 is determined as a non-function unit by the functional status determination unit 410, while the rest of the detector units are determined as functional units. The reconstruction data generation unit 420 may assign functional detector units into a first group, including detector unit 320, detector unit 330, detector unit 340, detector unit 350, detector unit 370, detector unit 380, and detector unit 390. The reconstruction data generation unit 420 may assign non-functional detector units into a second group, including detector unit 360. The reconstruction data generation unit 420 may further assign the detector units in the first group into subgroups based on their locations relative to the location of the non-functional detector unit 360. The reconstruction data generation unit 420 may further assign detector unit 320, detector unit 330, detector unit 340, and detector unit 350 into a first subgroup because these detector units are located together and not spatially separated by the non-functional detector unit 360. The reconstruction data generation unit 420 may assign detector unit 370, detector unit 380, and detector unit 390 into a second subgroup because these detector units are located together and not spatially separated by the non-functional detector unit 360. The reconstruction data generation unit 420 may determine the number of detector units of in each of the one or more subgroups, compare the numbers to identify the target sub-group that includes the most functional detector units that are located together and not spatially separated by the non-functional detector unit 360. Then the reconstruction data generation unit 420 may determine reconstruction data based on coincidence events counted by the detector unit(s) in the target subgroup. As illustrated, the first subgroup includes four functional detector units and the second subgroup includes three functional detector units. The reconstruction data generation unit 420 may determine reconstruction data based on coincidence events counted by detector unit pairs in the first subgroup, including C(1, 1), C(1, 2), C(1, 3), C(1, 4), C(2, 2), C(2, 3), C(2, 4) C(3, 3) C(3, 4), and C(4, 4).

In some embodiments, a scan object may be divided into one or more scan regions. When the table 114 is positioned at a table position, each of the one or more scan regions may correspond to at least one detector unit. A position of each of the one or more scan regions on the table 114 may also correspond to a spatial position of respective detector units. Coincidence events relating to a scan region corresponding to a non-functional detector unit (e.g., the detector unit 360) may be replaced by other coincidence events relating to the scan region counted by one or more other functional detector units in another PET scan performed when the table 114 is moved to a different table position. For example, by moving the table 114 or the PET scanner 112 along the z axis, the scan region corresponding to a non-functional detector unit may be moved to a position that corresponds to one or more functional detector units. The scan region now corresponding to a functional detector unit may then be scanned. PET data relating to the scan region may be obtained using the functional detector unit(s), and may replace the PET data relating to the scan region obtained in the previous PET scan.

For example, as shown in FIG. 7A, in a first PET scan, detector unit 360 is determined as a non-function detector unit, and a position of the table 114 may be referred to as table position 1 at this time. The table position may refer to a spatial position of the table 114. In some embodiments, a table position may be defined or described relative to an immobile portion, e.g., an immobile portion of the imaging section 110 (e.g., the detection region 113 of the imaging section 110), an immobile portion of the table 114 (e.g., an immobile base of the table 114), the floor on which the imaging section 110 or the table 114 sits. Coincidence events relating to a scan region corresponding to detector unit 360 may be excluded from the reconstruction data, including C(5,5), C(4,5), C(3,5), C(2,5), C(1,5). Then in a second PET scan, by moving the table 114 from the table position 1 to a table position 2, the scan region corresponding to detector unit 360 may be moved to a position that corresponding to detector unit 350, which is a functional detector unit. The table position 2 may be a position of table 114 when the scan region is corresponding to detector unit 350. Thus, coincidence events counted by the detector unit 330 and 340 in the second PET scan may replace coincidence event counted by the PET 350 and 340 (e.g. C(4, 5)). Coincidence events counted by the detector unit 320 and 340 in the second PET scan may replace coincidence event counted by the PET 350 and 330 (e.g. C(3, 5)). Coincidence events counted by the detector unit 310 and 340 in the second PET scan may replace coincidence event counted by the PET 350 and 320 (e.g. C(2, 5)). Based on a scan of each of the one or more scan regions by one or more function detector units, reconstruction data relating to the scan object may be obtained by performing data reorganization on coincidence events (also referred to as PET data) relating to the one or more scan regions. A PET image of the scan object may be obtained based on the reconstruction data.

Figures 8A, 8B:
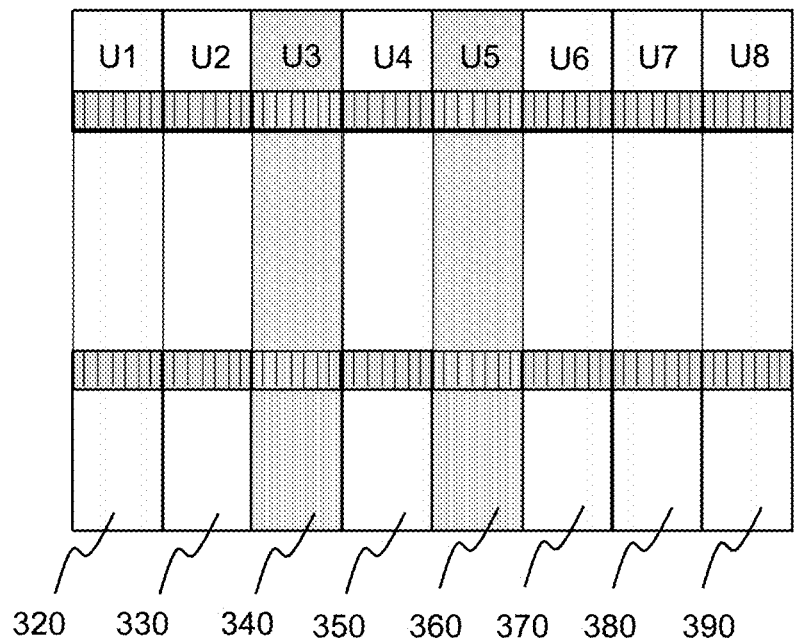
FIG. 8A is a schematic diagram illustrating a PET scanner with non-functional detector units.
FIG. 8B is an exemplary illustration of coincident events of the PET scanner illustrated in FIG. 8A.

FIG. 8A illustrates another exemplary PET scanner with non-functional detector units. FIG. 8B illustrates a map of detector unit pairs that detect coincident events. For example, C (6, 6) may represent one or more coincidence events counted by detector unit 370 and detector unit 370, and C (6, 7) may represent one or more coincidence events counted by detector unit 370 and detector unit 380, and so on.

As shown in FIG. 8A, detector unit 340 and detector unit 360 may be determined as non-function units by the functional status determination unit 410, while the rest of the detector units may be determined as functional units. The reconstruction data generation unit 420 may assign functional detector units into a first group, including detector unit 320, detector unit 330, detector unit 350, detector unit 370, detector unit 380, and detector unit 390. The reconstruction data generation unit 420 may assign non-functional detector units into a second group, including detector unit 340 and detector unit 360.

The reconstruction data generation unit 420 may further assign the detector units in the first group into subgroups based on their locations relative to the location of the non-functional detector unit 340 and 360. The reconstruction data generation unit 420 may further assign detector unit 320 and detector unit 330 into a first subgroup because these detector units are located together and not spatially separated by the non-functional detector unit 340 or 360. The reconstruction data generation unit 420 may assign detector unit 370, detector unit 380, and detector unit 390 into a second subgroup because these detector units are located together and not spatially separated by the non-functional detector unit 340 or 360. The reconstruction data generation unit 420 may then assign detector unit 350 into a third subgroup because detector unit 350 is not adjacent to any other functional detector unit in the first group.

The reconstruction data generation unit 420 may determine the number of detector units of in each of the one or more subgroups, compare the numbers to identify the target subgroup that includes the most functional detector units that are located together and not spatially separated by the non-functional detector unit 340 or 360. Then the reconstruction data generation unit 420 may determine reconstruction data based on coincidence events counted by the detector unit(s) in the target subgroup. As illustrated, the first subgroup includes two functional detector units, the second subgroup includes three functional detector units, and the third subgroup including one functional detector unit. The reconstruction data generation unit 420 may determine reconstruction data based on coincidence events counted by detector unit pairs in the second subgroup, including C (6, 6), C (6, 7), C (6, 8), C (7, 7), C (7, 8), and C (8, 8), as shown in FIG. 8B.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on at least one device each of which has at least one processor and storage, the method comprising:
   obtaining scan data relating to an object collected by a plurality of detector units;
   determining functional status of the plurality of detector units;
   dividing the plurality of detector units into a first group and a second group based on the functional status of the respective detector units, wherein the functional status of the detector units in the first group is functional, and the functional status of the detector units in the second group is non-functional;
   generating reconstruction data based on the scan data collected by the detector units in the first group; and
   reconstructing an image based on the reconstruction data.

2. The method of claim 1, wherein a detector unit of the plurality of detector units includes one or more PET detector rings.

3. The method of claim 1, wherein the reconstruction data includes a portion of the scan data that is collected by a first detector unit and a second detector unit of the plurality of detector units, a unit difference between the first detector unit and the second detector unit is less than a threshold.

4. The method of claim 3, wherein the unit difference represents an axial distance between the first detector unit and the second detector unit.

5. The method of claim 1, wherein determining functional status of a detector unit is determined based on a counting rate of the detector unit.

6. The method of claim 1, wherein the detector units in the first group are located side by side.

7. The method of claim 1, wherein the generating reconstruction data based on the functional status of the respective detector units and the scan data comprises:
dividing the detector units in the first group into more than one subgroup, wherein the detector units in each of the more than one subgroup are located side by side, and
generating the reconstruction data based on the scan data collected by the detector units in a subgroup of the more than one subgroup with the largest number of detector units.

8. The method of claim 1, wherein a detector unit of the plurality of detector units includes a plurality of detector subunits, and the determining functional status of the respective detector units further comprises:
for each detector unit of the plurality of detector units,
determining functional status of the respective detector subunits of a detector unit; and
determining functional status of the detector unit based on the functional status of the plurality of detector subunits of the detector unit.

9. A system, comprising:
at least one storage medium including a set of instructions; and
at least one processor configured to communicate with the at least one storage medium, wherein when executing the set of instructions, the system is configured to:
obtain scan data relating to an object collected by a plurality of detector units;
determine functional status of the plurality of detector units;
divide the plurality of detector units into a first group and a second group based on the functional status of the respective detector units, wherein the functional status of the detector units in the first group is functional, and the functional status of the detector units in the second group is non-functional;
generate reconstruction data based on the scan data collected by the detector units in the first group; and
reconstruct an image based on the reconstruction data.

10. The system of claim 9, wherein determining functional status of a detector unit is determined based on a counting rate of the detector unit.

11. The system of claim 9, wherein a detector unit of the plurality of detector units includes one or more PET detector rings.

12. The system of claim 9, wherein the reconstruction data includes a portion of the scan data that is collected by a first detector unit and a second detector unit of the plurality of detector units, a unit difference between the first detector unit and the second detector unit is less than a threshold.

13. The system of claim 12, wherein the unit difference represents an axial distance between the first detector unit and the second detector unit.

14. The system of claim 9, wherein a detector unit of the plurality of detector units includes a plurality of detector rings, and the determining functional status of the respective detector units further comprises:
for each detector unit of the plurality of detector units,
determining functional status of the respective detector subunits of a detector unit; and
determining functional status of the detector unit based on the functional status of the plurality of detector subunits of the detector unit.

15. The system of claim 9, wherein the detector units in the first group are located side by side.

16. The system of claim 9, wherein to generate reconstruction data based on the functional status of the respective detector unit and the scan data comprises:
dividing the detector units in the first group into more than one subgroup, wherein the detector units in each of the more than one subgroup are located side by side, and
generating the reconstruction data based on the scan data collected by the detector units in a subgroup of the more than one subgroup with the largest number of detector units.

17. A non-transitory computer readable medium storing instructions, the instructions, when executed by a computing device, causing the computing device to implement a method, comprising:
obtaining scan data relating to an object collected by a plurality of detector units;
determining functional status of the plurality of detector units;
dividing the plurality of detector units into a first group and a second group based on the functional status of the respective detector units, wherein the functional status of the detector units in the first group is functional, and the functional status of the detector units in the second group is non-functional;
generating reconstruction data based on the scan data collected by the detector units in the first group; and
reconstructing an image based on the reconstruction data.

* * * * *